(12) United States Patent
Yu

(10) Patent No.: US 10,537,235 B2
(45) Date of Patent: Jan. 21, 2020

(54) MULTIMODAL ENDOSCOPE APPARATUS

(71) Applicant: Bing Yu, Hudson, OH (US)

(72) Inventor: Bing Yu, Hudson, OH (US)

(73) Assignee: The University of Akron, Akron, OH (US)

(*) Notice: Subject to any disclaimer, the term of this patent is extended or adjusted under 35 U.S.C. 154(b) by 1191 days.

(21) Appl. No.: 14/824,535

(22) Filed: Aug. 12, 2015

(65) Prior Publication Data
US 2016/0045102 A1   Feb. 18, 2016

Related U.S. Application Data

(60) Provisional application No. 62/036,286, filed on Aug. 12, 2014.

(51) Int. Cl.
*A61B 1/07* (2006.01)
*A61B 5/00* (2006.01)
*A61B 1/04* (2006.01)

(52) U.S. Cl.
CPC ............ *A61B 1/07* (2013.01); *A61B 5/0035* (2013.01); *A61B 5/0095* (2013.01); *A61B 1/043* (2013.01)

(58) Field of Classification Search
CPC ... A61B 1/07; A61B 1/00126; A61B 1/00167; A61B 1/00172; A61B 1/043; A61B 5/0035; A61B 5/0095; A61B 5/0062; A61B 5/0066; A61B 5/0071; A61B 5/0086
See application file for complete search history.

(56) References Cited

U.S. PATENT DOCUMENTS

| | | | | |
|---|---|---|---|---|
| 6,485,413 B1 * | 11/2002 | Boppart | ............. | A61B 1/00096 356/450 |
| 2004/0195497 A1 * | 10/2004 | Sasaki | ................ | G01N 21/6458 250/234 |
| 2009/0021724 A1 * | 1/2009 | Mahadevan-Jansen | ..................... | A61B 5/0066 356/73 |

OTHER PUBLICATIONS

Bedard, et al. "Emerging roles for multimodal optical imaging in early cancer detection: a global challenge" Technol. Cancer Res. Treat, 9(2): p. 211-7 (2010).
Boppart, et al. "Optical imaging technology in minimally invasive surgery. Current status and future directions" Surg. Endosc., 13(7): p. 718-22 (1999).

(Continued)

*Primary Examiner* — Bo Joseph Peng
(74) *Attorney, Agent, or Firm* — Renner Kenner Greive Bobak Taylor & Weber

(57) ABSTRACT

A multimodal endoscope apparatus includes optical components (couplers, collimators, mirrors, beam splitters, filters and the like) structured to work together to interact with a multimodal endoscope probe to provide at least two imaging modalities selected from fluorescence imaging, optical coherence tomography, and photoacoustic imaging. The multimodal endoscope probe includes a fiber optic imaging bundle including a multitude of optical fibers. In embodiments employing photoacoustic imaging, the multimodal endoscope probe further includes a polymer-Fabry-Perot interferometer. In some embodiments, a galvo scanner and fiber collimator are included and are together capable of directing light to a single optical fiber of the multitude optical fibers. The system is modular in some embodiments, allowing for switching of some components.

13 Claims, 5 Drawing Sheets

(56) References Cited

OTHER PUBLICATIONS

Curvers, et al., "Endoscopic trimodal imaging versus standard video endoscopy for detection of early Barrett's neoplasia: a multicenter, randomized, crossover study in general practice", Gastrointest. Endosc., 73(2): p. 195-203 (2011).
Kirtane, et al., "Endoscopic Optical Coherence Tomography (OCT): Advances in Gastrointestinal Imaging", Gastroenterol. Res. Pract., vol. 2014, p. 1-7 (2014).
Mavadia, et al., "An all-fiber-optic endoscopy platform for simultaneous OCT and fluorescence imaging", Biomed. Opt. Express, 3(11): p. 2851-2859 (2012).
Pierce, et al., "High-resolution fiber-optic microendoscopy for in situ cellular imaging", J Vis Exp, (47), p. 1-5 (2011).
Shao, et al., "Integrated micro-endoscopy system for simultaneous fluorescence and optical-resolution photoacoustic imaging" J Biomed Opt, 17(7): p. 076024 (2012).
Xi, et al., "Integrated multimodal endomicroscopy platform for simultaneous en face optical coherence and two-photon fluorescence imaging" Opt Lett, 37(3): p. 362-364 (2012).
Yang, et al. "Integrated optical coherence tomography, ultrasound and photoacoustic imaging for ovarian tissue characterization" Biomed. Opt Express, 2(9): p. 2551-2561 (2011).
Yang, et al., "Simultaneous functional photoacoustic and ultrasonic endoscopy of internal organs in vivo" Nat Med, 18(8): p. 1297-1302 (2012).

\* cited by examiner

MULTIMODAL ENDOSCOPE APPARATUS

CROSS-REFERENCE TO RELATED APPLICATIONS

The present application is a Non-Provisional filing based on U.S. Provisional patent application Ser. No. 62/036,286, filed Aug. 12, 2014, the entirety of which is incorporated herein by reference.

FIELD OF THE INVENTION

The present invention generally relates to endoscope apparatus. More particularly, it relates to endoscope apparatus that provide multiple imaging functionalities, herein referred to as multimodal endoscope apparatus. In some embodiments, the present invention further relates to novel endoscope systems focusing on the employment of galvo scanners and fiber collimators in conjunction with Fabry-Perot interferometers on an endoscope probe.

BACKGROUND OF THE INVENTION

Optical imaging is a versatile and widely used visualization modality in modern medical research and clinical practice. The past few decades have witnessed an explosion in the development of various optical imaging technologies that currently exist. Fluorescence imaging (FLI) has been vastly improved to provide insight into the cellular structure and organization with a spatial resolution approaching that of electron microscopy. Optical coherence tomography (OCT), a twenty-year old technique that is based on low-coherence interferometry, enables the visualization of sub-surface anatomic structures of biological tissue with a resolution down to a few microns. In the past decade, photoacoustic imaging (PAI) has emerged as a promising medical imaging modality to delineate microvasculature and tissue physiological/functional parameters non-invasively at ultrasound resolution. All these imaging modalities have been successfully applied endoscopically for noninvasive and high resolution imaging of various internal structures and organs, such as the brain, gastrointestinal tract, vasculature, digestive tract, cervix, colon, bladder, ovary, kidney, etc. However, individually, these imaging modalities do not provide sufficient information to get an accurate clinical diagnosis, such as a cancerous development.

Recent years have also seen increasing research and development focused on integration of multiple imaging modalities into a single high resolution fiber optic endoscope [See Bedard, N., M. Pierce, A. El-Nagger, S. Anandasabapathy, A. Gillenwater, and R. Richards-Kortum, *Emerging roles for multimodal optical imaging in early cancer detection: a global challenge*. Technol Cancer Res Treat, 2010. 9(2): p. 211-7; and Boppart, S. A., T. F. Deutsch, and D. W. Rattner, *Optical imaging technology in minimally invasive surgery. Current status and future directions*. Surg Endosc, 1999. 13(7): p. 718-22].

Yang et al., reported the integration of OCT, ultrasound and PAI into a 5-mm endoscope for ovarian tissue characterization [See Yang, Y., X. Li, T. Wang, P. D. Kumavor, A. Aguirre, K. K. Shung, Q. Zhou, M. Sanders, M. Brewer, and Q. Zhu, *Integrated optical coherence tomography, ultrasound and photoacoustic imaging for ovarian tissue characterization*. Biomed Opt Express, 2011. 2(9): p. 2551-61].

Li et al., developed an all-fiber-optic endoscopy platform using a double-clad fiber for simultaneous OCT and fluorescence imaging [See Mavadia, J., J. Xi, Y. Chen, and X. Li, *An all-fiber-optic endoscopy platform for simultaneous OCT and fluorescence imaging*. Biomed Opt Express, 2012. 3(11): p. 2851-9; and Xi, J., Y. Chen, Y. Zhang, K. Murari, M. J. Li, and X. Li, *Integrated multimodal endomicroscopy platform for simultaneous en face optical coherence and two-photon fluorescence imaging*. Opt Lett, 2012. 37(3): p. 362-4].

Shao et al, designed an integrated microendoscopy system combining photoacoustic and fluorescence microscopy for visualizing fluorescently labeled cellular components and optically absorbing microvasculature simultaneously [See Shao, P., W. Shi, P. Hajireza, and R. J. Zemp, *Integrated micro-endoscopy system for simultaneous fluorescence and optical-resolution photoacoustic imaging*. J Biomed Opt, 2012. 17(7): p. 076024].

Yang et al., presented simultaneous functional photoacoustic and ultrasonic endoscopy of internal organs in vivo [See Yang, J. M., C. Favazza, R. Chen, J. Yao, X. Cai, K. Maslov, Q. Zhou, K. K. Shung, and L. V. Wang, *Simultaneous functional photoacoustic and ultrasonic endoscopy of internal organs in vivo*. Nat Med, 2012. 18(8): p. 1297-1302].

Most of the existing multimodal endoscopic imaging systems combine two imaging modalities, and, only a few attempts have been made to integrate all three modalities into a single fiber optic endoscope.

These existing multimodality techniques often require mechanical scanning at the distal end of the probe, which is challenging largely due to the size constraints and is often incompatible with widely used whole body imaging procedures, such as magnetic resonance imaging (MRI) and computerized tomography (CT). A major difficulty in developing a multimodality endoscope that includes PAI is to design an ultrasonic detector array that fits a tight space with enough detection bandwidth and sensitivity for the recovery of weak photoacoustic signals. In addition, a compact endoscopic imaging platform that accommodates or can be easily modified for all three imaging modalities has not been reported. The ability to provide complimentary, high resolution images about tissue structural, functional and molecular information with a single endoscope would substantially improve the sensitivity and specificity in diagnosis and characterization of a variety of disorders, such as the detection of pre-cancers lesions and cancers.

SUMMARY OF THE INVENTION

In a first embodiment, the present invention provides a multimodal endoscope apparatus comprising a multimodal endoscope probe including a fiber optic imaging bundle including a multitude of optical fibers, a galvo scanner and fiber collimator that are together capable of directing light to a single optical fiber of multitude optical fibers, an optical coherence tomography system launching a swept laser to the galvo scanner, and a fluorescence imaging system including a fluorescence excitation system launching a fluorescence excitation laser to the galvo scanner, and a fluorescence emission system receiving a reflected fluorescence emission from the multimodal endoscope probe.

In a second embodiment, the present invention provides a multimodal endoscope apparatus as in the first embodiment, wherein the fluorescence excitation system further includes a fluorescence excitation laser source directing the fluorescence excitation laser to the galvo scanner.

In a third embodiment, the present invention provides a multimodal endoscope apparatus as in either the first or second embodiment, wherein the fluorescence excitation laser has a wavelength below λ1, and the fluorescence excitation laser source directs the fluorescence excitation laser to a first beamsplitter, which blocks wavelengths below λ3 and allows for passage of wavelengths above λ3, wherein λ1 is less than λ3 such that the fluorescence excitation laser is reflected by the first beamsplitter to the galvo scanner.

In a fourth embodiment, the present invention provides a multimodal endoscope apparatus as in any of the first through third embodiments, wherein the fluorescence excitation laser source directs the fluorescence excitation laser to a second beamsplitter, which blocks wavelengths below λ2 and allows for passage of wavelengths above λ2, wherein λ1 is less than λ2 such that the fluorescence excitation laser is reflected by the second beamsplitter to the first beamsplitter.

In a fifth embodiment, the present invention provides a multimodal endoscope apparatus as in any of the first through fourth embodiments, wherein the fluorescence excitation laser source directs the fluorescence excitation laser to a third beamsplitter, which blocks wavelengths below λ1 and allows for passage of wavelengths above λ1, such that the fluorescence excitation laser is reflected by the first beamsplitter to the second beamsplitter.

In a sixth embodiment, the present invention provides a multimodal endoscope apparatus as in any of the first through fifth embodiments, wherein the reflected fluorescence emission from the multimodal endoscope probe is directed back to the galvo scanner through the fiber optic imaging bundle and, from the galvo scanner, back to an image sensor or spectrometer.

In a seventh embodiment, the present invention provides a multimodal endoscope apparatus as in any of the first through sixth embodiments, wherein the reflected fluorescence emission has a wavelength of from λ1 to λ2 and is directed by the galvo scanner to the first dichroic beamsplitter, λ2 is less than λ3 such that the reflected fluorescence emission is reflected by the first beamsplitter.

In an eighth embodiment, the present invention provides a multimodal endoscope apparatus as in any of the first through seventh embodiments, wherein the reflected fluorescence emission is reflected by the first dichroic beamsplitter to the second dichroic beamsplitter, such that the reflected fluorescence emission is reflected by the second dichroic beamsplitter.

In a ninth embodiment, the present invention provides a multimodal endoscope apparatus as in any of the first through eighth embodiments, wherein the reflected fluorescence emission is reflected by the second dichroic beamsplitter to a third dichroic beamsplitter, which blocks wavelengths below λ1 and allows for passage of wavelengths above λ1, such that the reflected fluorescence emission passes through the first dichroic beamsplitter.

In a tenth embodiment, the present invention provides a multimodal endoscope apparatus as in any of the first through ninth embodiments, wherein the optical coherence tomography system further includes a swept laser source.

In an eleventh embodiment, the present invention provides a multimodal endoscope apparatus as in any of the first through tenth embodiments, wherein the optical coherence tomography system includes an optical coherence tomography detector.

In a twelfth embodiment, the present invention provides a multimodal endoscope apparatus as in any of the first through eleventh embodiments, wherein the swept laser is split at a coupler and directed (1) through a sample arm of the optical coherence tomography system to the galvo scanner, and (2) through a reference arm of the optical coherence tomography system directing light to a mirror for reflection back to the optical coherence tomography detector.

In a thirteenth embodiment, the present invention provides a multimodal endoscope apparatus as in any of the first through twelfth embodiments, wherein the swept laser has a wavelength of from λ3 to λ4, and the swept laser in the sample arm is directed to the first dichroic beamsplitter on a path to the galvo scanner, wherein λ3 is less than λ4 such that the swept laser is reflected by the third dichroic beamsplitter.

In a fourteenth embodiment, the present invention provides a multimodal endoscope apparatus as in any of the first through thirteenth embodiments, wherein the swept laser in the sample arm is directed to a fourth dichroic beamsplitter, wherein the fourth dichroic beamsplitter blocks wavelengths below λ4 and allows for passage of wavelengths above λ4 such that the swept laser is reflected by the fourth dichroic beamsplitter toward the first dichroic beamsplitter.

In a fifteenth embodiment, the present invention provides a multimodal endoscope apparatus as in any of the first through fourteenth embodiments, wherein the path of the swept laser from the swept laser source through the reference arm and back to the optical coherence tomography detector matches the length of the path of the swept laser from the swept laser source through the sample arm and to and through the multimodal endoscope probe to contact with a tissue and back to the optical coherence tomography detector.

In a sixteenth embodiment, the present invention provides a multimodal endoscope apparatus as in any of the first through fifteenth embodiments, wherein the multimodal endoscope probe includes a Fabry-Perot interferometer abutting a distal end of a fiber optic imaging bundle including a multitude of optical fibers, the Fabry-Perot interferometer including a polymer film sandwiched between a first dielectric mirror and a second dielectric mirror, wherein the first and second dielectric mirrors are transparent to the wavelengths produced from the optical coherence tomography system and the fluorescence imaging system.

In a seventeenth embodiment, the present invention provides a multimodal endoscope apparatus as in any of the first through sixteenth embodiments, wherein further comprising a photoacoustic imaging system including a photoacoustic excitation system launching a pulsed laser to the galvo scanner, and a photoacoustic detection system launching a interrogating laser to the galvo scanner.

In an eighteenth embodiment, the present invention provides a multimodal endoscope apparatus as in any of the first through seventeenth embodiments, wherein the first and second dielectric mirrors reflect a portion of wavelengths from the interrogating laser.

In a nineteenth embodiment, the present invention provides a multimodal endoscope apparatus as in any of the first through eighteenth embodiments, wherein the photoacoustic excitation system includes a pulsed laser source directing the pulsed laser to the galvo scanner.

In a twentieth embodiment, the present invention provides a multimodal endoscope apparatus as in any of the first through nineteenth embodiments, wherein the pulsed laser has a wavelength of from λ2 to λ3, and the pulsed laser source directs the pulsed laser to the first dichroic beamsplitter, such that the pulsed laser is reflected by the first dichroic beamsplitter to the galvo scanner.

In a twenty-first embodiment, the present invention provides a multimodal endoscope apparatus as in any of the first through twentieth embodiments, wherein the pulsed laser source directs the pulsed laser to the second dichroic beamsplitter, such that the pulsed laser passes through the second dichroic beamsplitter to the first dichroic beamsplitter.

In a twenty-second embodiment, the present invention provides a multimodal endoscope apparatus as in any of the first through twenty-first embodiments, wherein the photoacoustic detection system includes an interrogating laser source directing the interrogating laser to the galvo scanner.

In a twenty-third embodiment, the present invention provides a multimodal endoscope apparatus as in any of the first through twenty-second embodiments, wherein the interrogating laser has a wavelength of greater than λ4, and the interrogating laser source directs the interrogating laser to the first dichroic beamsplitter, wherein λ4 is greater than λ3 such that the interrogating laser passes through the first dichroic beamsplitter to the galvo scanner.

In a twenty-fourth embodiment, the present invention provides a multimodal endoscope apparatus as in any of the first through twenty-third embodiments, wherein the interrogating laser source directs the interrogating laser to the fourth dichroic beamsplitter such that the interrogating laser passes through the fourth dichroic beamsplitter to the first dichroic beamsplitter.

In a twenty-fifth embodiment, the present invention provides a multimodal endoscope apparatus as in any of the first through twenty-fourth embodiments, wherein the photoacoustic detection system further comprises an amplified InGaAs photodiode, and the interrogating laser is received by the amplified InGaAs photodiode.

In a twenty-sixth embodiment, the present invention provides a multimodal endoscope apparatus comprising a multimodal endoscope probe including a Fabry-Perot interferometer abutting a distal end of a fiber optic imaging bundle including a multitude of optical fibers, the Fabry-Perot interferometer including a polymer film sandwiched between a first dielectric mirror and a second dielectric mirror, a photoacoustic imaging system including a photoacoustic excitation system launching a pulsed laser to the multimodal endoscope probe, and a photoacoustic detection system launching a interrogating laser to the multimodal endoscope probe, an optical coherence tomography system launching a swept laser to the multimodal endoscope probe, and a fluorescence imaging system including a fluorescence excitation system launching a fluorescence excitation laser to the multimodal endoscope probe, and a fluorescence emission system receiving a reflected fluorescence emission from the multimodal endoscope probe, wherein the first and second dielectric mirrors are transparent to the wavelengths produced from the optical coherence tomography system and the fluorescence imaging system, and wherein the first and second dielectric mirrors reflect a portion of wavelengths from the interrogating laser. Any of the foregoing embodiments might also be incorporated with this embodiment.

In a twenty-seventh embodiment, the present invention provides a multimodal endoscope apparatus as in the twenty-sixth embodiment, further comprising a component platform to which is secured the photoacoustic excitation system, the photoacoustic detection system, the optical coherence topography system, the fluorescence excitation system, and the fluorescence emission system, wherein the photoacoustic excitation system includes a pulsed laser source removably connected to the component platform at a pulsed laser source connector such that the pulse laser source can be selectively switched out for a separate pulsed laser source of differing wavelength, the photoacoustic detection system includes an interrogating laser source removably connected to the component platform at an interrogating laser source connector such that the interrogating laser source can be selectively switched out for a separate interrogating laser source of differing wavelength, the photoacoustic detection system includes an amplified InGaAs photodiode removably connected to the component platform at a photodiode connector such that the amplified InGaAs photodiode can be selectively switched out for a separate optical coherence topography detector of different bandwidth or gain, the optical coherence tomography system includes a swept laser source removably connected to the component platform at a swept laser source connector such that the swept laser source can be selectively switched out for a separate swept laser source of differing wavelength, the optical coherence tomography system includes an optical coherence tomography detector removably connected to the component platform at a detector connector such that the optical coherence topography detector can be selectively switched out for a separate optical coherence topography detector of different bandwidth or gain, and the fluorescence excitation system further includes a fluorescence excitation laser source removably connected to the component platform at a fluorescence excitation laser source connector, such that the fluorescence excitation laser source can be selectively switched out for a separate fluorescence excitation laser source of differing wavelength. Any of the foregoing embodiments might also be incorporated with this embodiment.

In a twenty-eighth embodiment, the present invention provides a multimodal endoscope apparatus comprising a galvo scanner, a fiber collimator, a multimodal endoscope probe including a Fabry-Perot interferometer abutting a distal end of a fiber optic imaging bundle including a multitude of optical fibers, the Fabry-Perot interferometer including a polymer film sandwiched between a first dielectric mirror and a second dielectric mirror, a photoacoustic imaging system including a photoacoustic excitation system launching a pulsed laser to the galvo scanner, and a photoacoustic detection system launching a interrogating laser to the galvo scanner, wherein the galvo scanner and the fiber collimator are together capable of directing light to a single optical fiber of the multitude of optical fibers. Any of the foregoing embodiments might also be incorporated with this embodiment.

In a twenty-ninth embodiment, the present invention provides a multimodal endoscope probe comprising a Fabry-Perot interferometer abutting a distal end of a fiber optic imaging bundle including a multitude of optical fibers, the Fabry-Perot interferometer including a polymer film sandwiched between a first dielectric mirror and a second dielectric mirror, the first and second dielectric mirrors being (a) transparent to the wavelength of a photoacoustic excitation laser, (b) transparent to the wavelength of an optical coherence tomography swept laser, and (c) transparent to a fluorescence excitation laser, and (d) transparent to a reflected fluorescence emission produced by the fluorescence excitation laser, and the first and second dielectric mirrors reflecting a portion of a photoacoustic interrogation laser. Any of the foregoing embodiments might also be incorporated with this embodiment.

DETAILED DESCRIPTION OF ILLUSTRATIVE EMBODIMENTS

Figure 1:
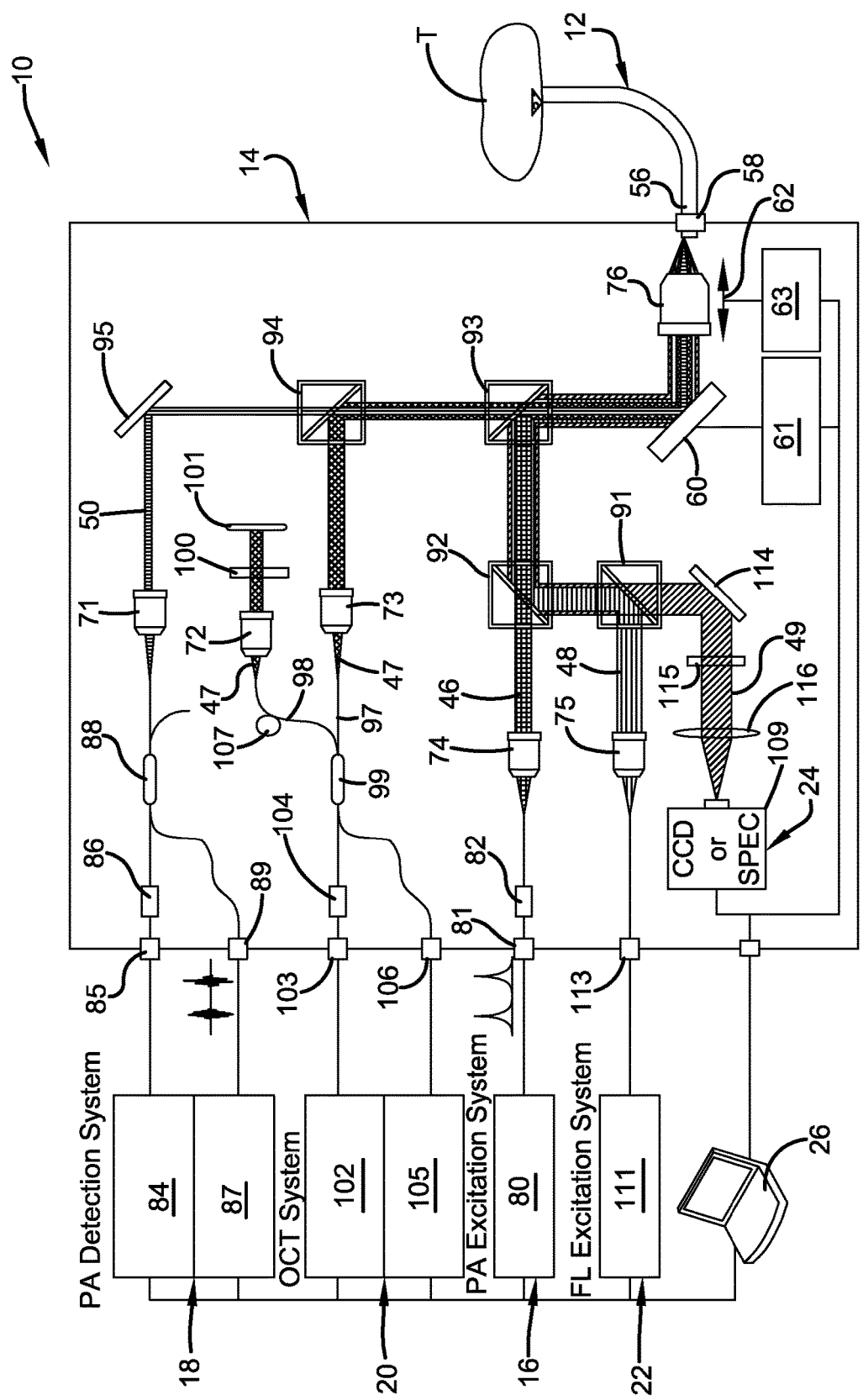
FIG. 1 is a schematic representation of an embodiment of a multimodal endoscope apparatus according to this invention, shown with all modalities (photoacoustic imaging, OCT imaging, and fluorescence imaging) disclosed herein.

With reference to FIG. 1, a multimodal endoscope apparatus according to this invention is shown and designated by the numeral 10. The apparatus 10 includes a multimodal endoscope probe 12 and a component platform 14. The component platform 14 serves to house many optical components (couplers, collimators, mirrors, beam splitters, filters, galvo scanner, CCD camera, etc.) that work together to provide various systems providing various functionalities—namely, a photoacoustic excitation system (or PA excitation system) 16, a photoacoustic detection system (or PA detection system) 18, an optical coherence tomography system (or OCT system) 20, a fluorescence excitation system (or FL excitation system) 22, and fluorescence emission system (or FL emission system) 24.

The PA excitation system 16 and PA detection system 18 communicate with a processor 26 suitable for controlling the operation of the two systems 16, 18 and collecting and processing data necessary to provide photoacoustic imaging. In some embodiments, the OCT system 20 also communicates with the processor 26, which is suitable for controlling the operation of the OCT system and collecting and process data necessary for OCT imaging, though in other embodiments, the control of the OCT system and the OCT imaging could be performed by a processor separate from processor 26. The FL excitation system 22 and FL emission system 24 also communicate with the processor 26, which is suitable for controlling the operation of the FL excitation and FL emission systems 22, 24 and collecting and process data necessary for fluorescence imaging, though in other embodiments, the control of the FL excitation and FL emission systems 22, 24 and the fluorescence imaging could be performed by a processor separate from processor 26.

In some embodiments, such as that shown in apparatus 10, the apparatus provides for three modalities of operation by having all of the PA excitation system 16, the PA detection system 18, the OCT system 20, the FL excitation system 22, and the FL emission system 24 communicate with the multimodal endoscope probe 12—thus providing for photoacoustic imaging, OCT imaging and fluorescence imaging in one apparatus.

Figure 2:
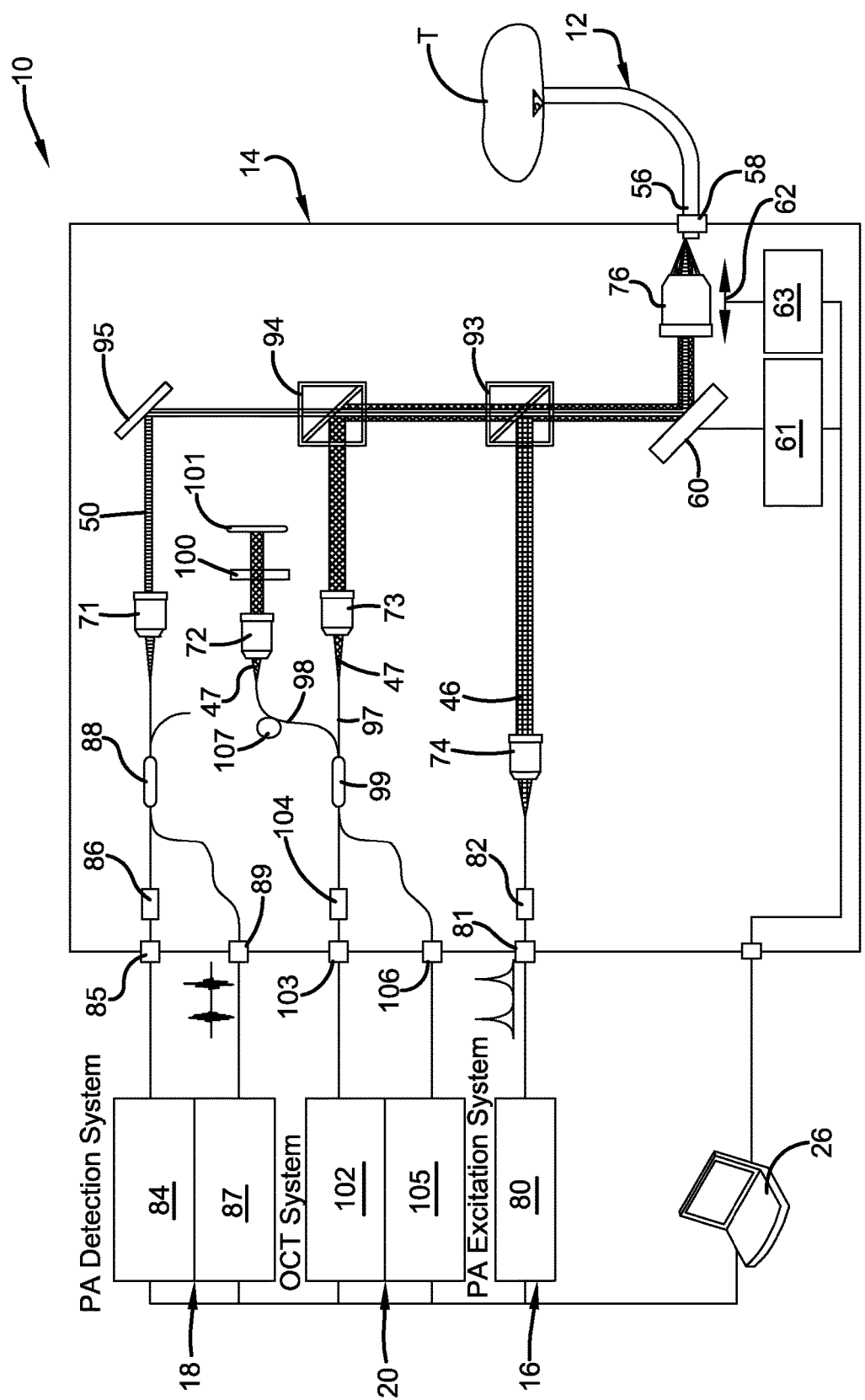
FIG. 2 is a schematic representation of an embodiment of a multimodal endoscope apparatus similar to that of FIG. 1, but lacking the fluorescence imaging modality.
Figure 3:
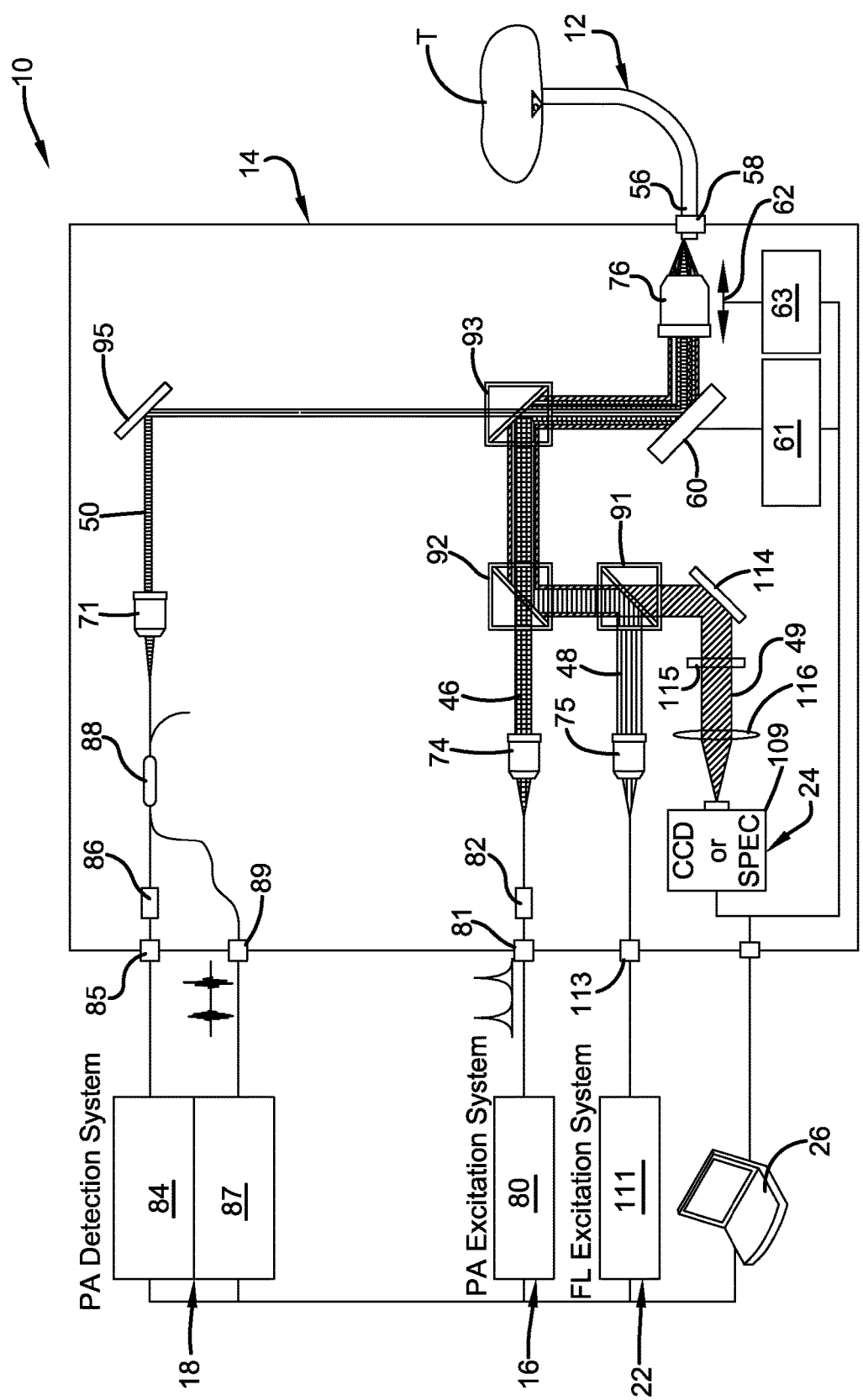
FIG. 3 is a schematic representation of an embodiment of a multimodal endoscope apparatus similar to that of FIG. 1, but lacking the OCT imaging modality.
Figure 4:
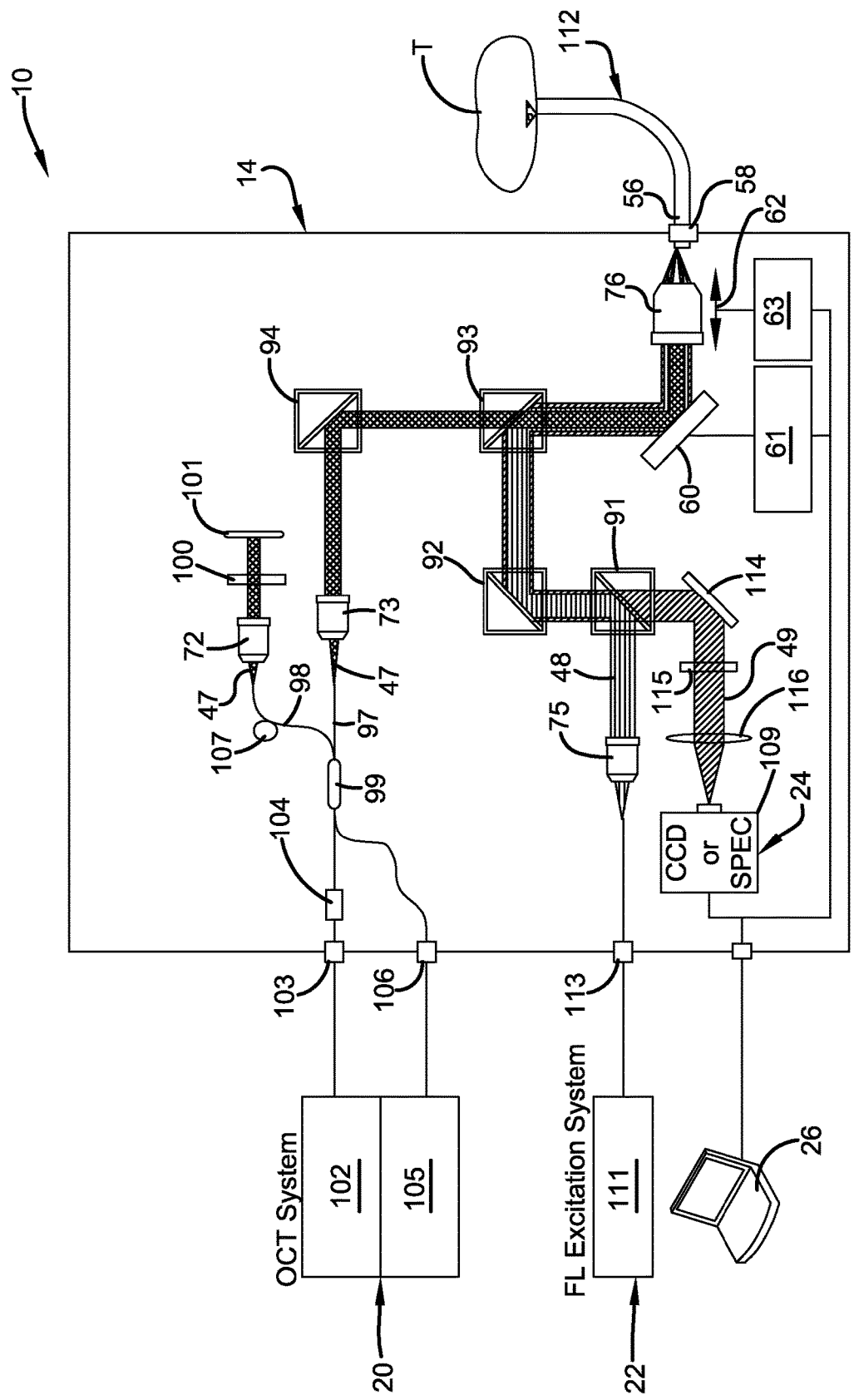
FIG. 4 is a schematic representation of an embodiment of a multimodal endoscope apparatus similar to that of FIG. 1, but lacking the photoacoustic imaging modality.

In some embodiments, the apparatus provides at least two of the imaging modalities—i.e., at least two of photoacoustic imaging, OCT imaging, and fluorescence imaging. This is shown in FIGS. 2 through 4. The apparatus 210 of FIG. 2 includes the PA excitation system 16, the PA detection system 18, and the OCT system 20 so as to provide for photoacoustic imaging and OCT imaging, but does not include the FL excitation system 22 and FL emission system 24. The apparatus 310 of FIG. 3 includes the PA excitation system 16, the PA detection system 18, the FL excitation system 22, and FL emission system 24 so as to provide for photoacoustic imaging and fluorescence imaging, but does not include the OCT system 20. The apparatus 410 of FIG. 4 includes the FL excitation system 22, the FL emission system 24, and the OCT system 20 so as to provide for fluorescence imaging and OCT imaging, but does not include the PA excitation system 16 and the PA detection system 18. It will be noted that like parts have received like numerals among the embodiments of FIGS. 2 through 4, and this is because those elements are the same. The only distinction is the type of probe that might be employed, and this distinction is noted by designating the multimodal endoscopic probe by the numeral 112 in FIG. 4.

Figure 5:
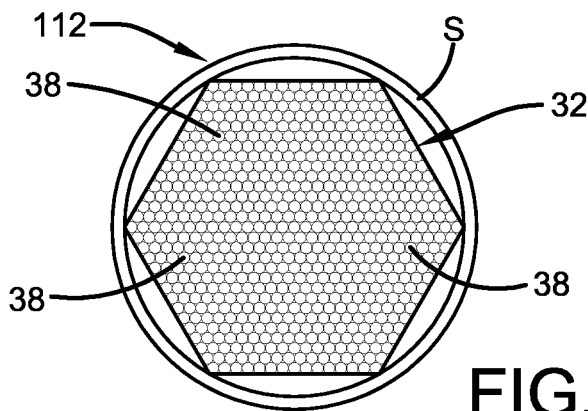
FIG. 5 is schematic representation of the fiber bundle of the endoscope probes of this invention.

In embodiments not employing photoacoustic imaging—i.e., those not employing the PA excitation system 16 and PA detection system 18—the multimodal endoscope probe 112 is employed, and, as seen in FIG. 5, is basically a coherent fiber optic imaging bundle 32 with appropriate sleeve S. Although FIG. 5 depicts the fiber optic imaging bundle 32 as hexagonal in shape, it should be appreciated that in some embodiments, the fiber optic imaging bundle 32 may also be circular in shape. The use of a hexagonal shape was merely easy for drawing purposes.

In embodiments employing photoacoustic imaging—i.e., those employing the PA excitation system 16 and PA detection system 18 to provide for photoacoustic imaging—the multimodal endoscope probe 12 is employed, and it includes a polymer Fabry-Perot interferometer 30 (FIG. 6) at a distal end thereof in contact with a target biological tissue T (e.g. FIG. 1). In a particular embodiment, the present invention provides a multimodal endoscope system including a PA excitation system, a PA detection system, an OCT system, a FL excitation system, and a FL emission system configured to interact with the multimodal endoscopic probe and selectively operate to provide PA imaging, OCT imaging, and fluorescence imaging of the target tissue in contact with the polymer Fabry-Perot interferometer.

Figure 6:
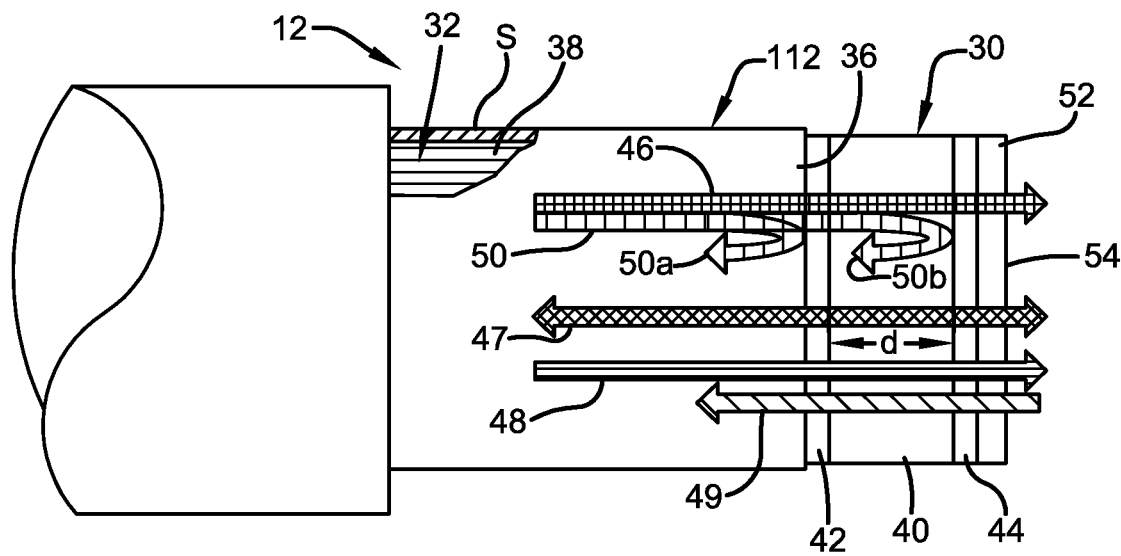
FIG. 6 is a schematic representation of a distal end of a multimodal endoscope probe used in some embodiments of this invention, particularly showing use of a Fabry-Perot interferometer.

As shown in FIG. 6, the multimodal endoscope probe 12 is basically a coherent fiber optic imaging bundle 32 (as described with respect to probe 112) with a polymer Fabry-Perot interferometer (P-FPI) 30 abutting the distal end 36 of the imaging bundle 32. The imaging bundle 32 includes thousands or tens of thousands of individual optical fibers 38 of a few to tens of micrometers in diameter. The P-FPI 30 is formed by a polymer film 40 sandwiched between a first dielectric mirror 42 and a second dielectric mirror 44. In some embodiments, the polymer film 40 is less than 100 micrometers thick (from first dielectric mirror 42 to second dielectric mirror 44). In other embodiments, the polymer film 40 is less than 90 micrometers thick, in other embodiments, less than 80 micrometers thick, in other embodiments, less than 70 micrometers thick, in other embodiments, less than 60 micrometers thick, in other embodiments, less than 50 micrometers thick, in other embodiments, less than 40 micrometers thick, in other embodiments, less than 30 micrometers thick, in other embodiments, less than 20 micrometers thick, in other embodiments, less than 15 micrometers thick, and in other embodiments, less than 10 micrometers thick.

In some embodiments, the polymer film 40 is greater than 10 micrometers thick (from first dielectric mirror 42 to second dielectric mirror 44). In other embodiments, the polymer film 40 is greater than 15 micrometers thick, in other embodiments, greater than 20 micrometers thick, in other embodiments, greater than 30 micrometers thick, in other embodiments, greater than 40 micrometers thick, in other embodiments, greater than 50 micrometers thick, in other embodiments, greater than 60 micrometers thick, in other embodiments, greater than 70 micrometers thick, in other embodiments, greater than 80 micrometers thick, and in other embodiments, greater than 90 micrometers thick.

In some embodiments, the polymer film 40 is from 10 or more to 100 or less micrometers thick. In other embodiments, the polymer film 40 is from 20 or more to 90 or less micrometers thick, in other embodiments, in other embodiments, from 25 or more to 80 or less micrometers thick, in other embodiments, from 30 or more to 70 or less micrometers thick, in other embodiments, from 35 or more to 60 or less micrometers thick, and in other embodiments, from 40 or more to 50 or less micrometers thick.

The first and second dielectric mirrors 42, 44 are transparent to the wavelengths of the photoacoustic excitation laser 46 of the photoacoustic excitation system 16, the OCT light 47 of the OCT system 20, the fluorescence excitation light 48 of the FL excitation system 22, and the fluorescence emission light 49 of the FL emission system 24, but these mirrors 42, 44 reflect a significant portion of wavelengths of the interrogating laser 50 back to one or more optical fibers 38 of the fiber optic bundle 32, as illustrated in FIG. 6. In some embodiments, 95% or less of the light transmitted to the P-FPI 30 by the photoacoustic detection interrogating laser 50 is reflected, in some embodiments, 90% or less, in some embodiments, 85% or less, in other embodiments, 80% or less, in other embodiments, 75% or less, in some embodiments, 70% or less, and in other embodiments, 65% or less. In some embodiments, 50% or more of the light transmitted to the P-FPI 30 by the photoacoustic detection interrogating laser 50 is reflected, in other embodiments, 55% or more, in some embodiments, 60% or more, in some embodiments, 65% or more, in some embodiments, 70% or more, in some embodiments 75% or more, and, in some embodiments, 80% or more. In other embodiments, the reflectivity is 50% or more to 95% or less.

The polymer film 40 can be formed of any polymer that transparent to all light in the visible and near-infrared band (400-1600 nm) and is chosen to be stiff enough to maintain its thickness without external pressure or acoustic wave applied. It is also chosen to be flexible so that the applied photoacoustic wave can cause a compression on the order of a few nanometers up to 1.0 um.

A protective layer 52 is used to protect the second dielectric mirror 44 from mechanical scratch or chemical/biological corrosion. This protective layer 52 is also formed of a polymer that is transparent to all light in the visible and near-infrared band (400-1600 nm). Because it provides protection, in some embodiments the protective layer 52 is chosen to be strong enough that it does not deform under the photoacoustic waves. Because this protective layer 52 comes into contact with tissue, it is also chosen to be biocompatible (e.g., $SiO_2$) in some embodiments. In some embodiments, the protective layer 52 is formed of a biocompatible polymer.

The distal end 54 of the P-FPI 30 is brought in contact with a target biological tissue T during imaging, and the proximal end 56 of the probe 12 is plugged into a fiber optic connector 58 (FC or SMA) on the component platform 14, to communicate with as shown in FIGS. 1 through 3. In the embodiment of FIG. 4, the probe 112 is also similarly connected by a connector 58.

As already noted, embodiments of this invention employ the necessary systems (16, 18, 20, 22, 24) to provide for any two of or all three of the modalities described here—photoacoustic imaging, OCT imaging, and fluorescence imaging. In some embodiments, the light from all systems share a galvo scanner 60 for scanning across optical fibers of the probe 12 (or 112) and a fiber collimator 76 to focus the lights into a single optical fiber 38 of the imaging bundle 32 or to collimate the lights returned from the distal end of the bundle 32. All three types of images (PAI, OCT and FLI) can be taken either in parallel—provided that the total laser energy is under the maximum permissible exposure (MPE)—or sequentially. Fiber collimator 76 is mounted on a motorized linear stage 62 so that the focus can be slightly tuned for different wavelength ranges, if necessary, in a sequential imaging mode.

In some embodiments, the sequential imaging mode will be found to be very beneficial. This mode involves the fiber-by-fiber (or pixel-by-pixel) scanning of the individual fibers 38 of the fiber bundle 32 through appropriate programming and control by processor 26 (or a separate processor). The processor 26 through appropriate combinations of any of hardware, software, firmware and the like, can be used to adjust the fiber collimator 76 by moving the linear stage 62 through motion controller 63 to focus the incoming light into a narrow enough beam that only a single fiber 38 is illuminated. The processor 26 (hardware/software/firmware/etc), through a driver 61, controls the galvo scanner 60 to pivot it at appropriate times and to the appropriate position to move the beam to a new fiber 38. After the imaging data is obtained for a given fiber 38, a new fiber 38 can be assessed and so on to obtain the imaging desired. The fiber collimator 76 can also move so as to defocus the beam and light up multiple or all of the fibers 38 of the fiber bundle 32, and the galvo scanner can be used to move that wider beam around.

It will be appreciated from FIGS. 1-4 and disclosures above and below that the P-FPI 30 is necessary and employed only when photoacoustic imaging is desired. The photoacoustic excitation system 16 launches a nanosecond laser pulse with a wavelength between $\lambda 2$ and $\lambda 3$ (e.g. at 850 nm), represented by pulsed laser 46. The pulsed laser 46 is focused into an optical fiber 38 of the fiber bundle 32 as directed by the galvo scanner 60, and propagates into the tissue through the probe 12 and the P-FPI 30, through the polymer film 40 and the protective layer 52, and the first and second dielectric mirrors 42, 44. The tissue T, under the active fiber 38 (pixel) absorbs the laser pulse and generates ultrasonic waves due to transient thermoelastic expansion. The acoustic pressure modulates the thickness of the polymer film 40 between the first and second dielectric mirrors 42, 44, and thus the distance "d" between first and second dielectric mirrors 42, 44, at a frequency up to tens of MHz.

The pulsed laser source 80 is connected to component platform 14 at connector 81, and the pulsed laser 46 is directed through an isolator 82 that prevents light coming back to the source 80. The pulsed laser 46 is directed through a fiber collimator 74 toward a dichroic beamsplitter 93. In embodiments employing fluorescence imaging (FL excitation system and FL emission system; FIG. 1, 3, 4), the pulsed laser 46 first passes through a dichroic beamsplitter 92 on its path to dichroic beamsplitter 93, the dichroic beamsplitters 92, 93 being aligned, as shown. The dichroic beamsplitter 92 is not needed when fluorescence imaging is not part of the apparatus (see FIG. 2). The dichroic beamsplitter 92 is a longpass filter blocking wavelengths below λ2 and allowing for passage of wavelengths above λ2. The dichroic beamsplitter 93 is a longpass filter blocking wavelengths below λ3 and allowing for passage of wavelengths above λ3. Thus, the pulsed laser 46 of wavelength between λ2 and λ3 reaches the galvo scanner 60 after being reflected by the dichroic beamsplitter 93 aligned with the galvo scanner 60.

The P-FPI 30 is interrogated by the photoacoustic detection system 18. The photoacoustic detection system 18 launches a tunable laser at a wavelength above λ4 (e.g., 1260-1360 nm), represented by interrogating laser 50. The interrogating laser 50 is focused into an optical fiber 38 of the fiber bundle 32 as directed by the galvo scanner 60, and propagates to the P-FPI 30 where a large portion is reflected back by the first and second dielectric mirrors 42, 44. As noted, the tissue T, under the active fiber 38 (pixel) absorbs the pulsed laser 46 from the PA excitation system 16, and this modulates the distance "d" between first and second dielectric mirrors 42, 44. The change in this distance is analyzed by the PA detection system 18.

The tunable laser source 84 is connected to component platform 14 at connector 85, and the interrogating laser 50 is directed through an isolator 86 that prevents light coming back to the source 84. The light does, however, come back to an amplified InGaAs photodiode 87 at coupler 88, the amplified InGaAs photodiode 87 connects to the component platform 14 at connector 89. The interrogating laser 50 is directed through a fiber collimator 71 toward a mirror 95 reflecting the interrogating laser 50 toward and through the dichroic beamsplitter 93 to the galvo scanner 60 where it is directed to the same fiber 38 or fibers 38 being excited by the PA excitation system 16. Notably, the mirror 95 could be removed by repositioning the tunable laser source 84 to direct the interrogating laser 50 directly to the galvo scanner 60, but in some embodiments, the mirror 95 is employed so that all of the systems 16, 18, 20, 22 can be connected at a common side of the component platform 14. In embodiments employing OCT imaging (OCT system 20; FIGS. 1, 2, 4), the interrogating laser 50 first passes through a dichroic beamsplitter 94 on its path to dichroic beamsplitter 93, the dichroic beamsplitters 94, 93 being aligned, as shown. The dichroic beamsplitter 94 is not needed when OCT imaging is not part of the apparatus (see FIG. 3). The dichroic beamsplitter 94 is a longpass filter blocking wavelengths below λ4 and allowing for passage of wavelengths above λ4. The dichroic beamsplitter 93 is a longpass filter blocking wavelengths below λ3 and allowing for passage of wavelengths above λ3. Thus, the interrogating laser 50 of wavelength above λ4 reaches the galvo scanner 60 after passing through the dichroic beamsplitter 93 aligned with the galvo scanner 60.

The interrogating laser 50 is reflected back from first and second dielectric mirrors 42, 44, of the Fabry-Perot interferometer. The laser beams 50a, 50b reflected by the two mirrors (FIG. 6) interfere with each other to form an interferogram when the laser wavelength is scanned. This interferogram travels back to the amplified InGaAs photodiode 87 where it is converted to an electrical signal. Then the laser wavelength is locked to one of the highest peak in the derivative of the interferogram. When there is no acoustic wave or outside pressure applied to the distal tip of the endoscope, the amplified photodiode outputs a constant current (or voltage). The ultrasound waves generated by the PA excitation laser 46 inside the tissue T impact on the protective layer 52 and cause oscillations in the thickness of the polymer film 40, which is translated as oscillations in the output of the amplified photodiode (photoacoustic signals).

The photoacoustic signals are analyzed by the processor 26 (or other processor) to construct a photoacoustic image about the tissue under the endoscope tip.

The OCT system 20 includes a swept laser source 102 that launches a swept laser with a wavelength between λ3 and λ4 (e.g. at 1060 nm), represented by swept laser 47. The swept laser 47 is split into a sample arm 97 and a reference arm 98 at coupler 99, and the swept laser 47 in the sample arm 97 is focused into an optical fiber 38 of the fiber bundle 32 as directed by the galvo scanner 60, and propagates into the tissue through the probe 12 or 112. The swept laser 47 in the reference arm 98 is directed through a fiber collimator 72 then through a neutral density (ND) filter 100 to reflect off of a mirror 101. The reflection is then directed back to an OCT detector 105 connected to the component platform 14 at connector 106.

The swept laser source 102 is connected to component platform 14 at connector 103, and the swept laser 47 is directed through an isolator 104 that prevents light coming back to the source 102. The swept laser 47 directed through the sample arm 97 is directed through a fiber collimator 73 toward a dichroic beamsplitter 94. In embodiments employing photoacoustic imaging (PA excitation system 16, and particularly PA detection system 18; FIG. 1, 2, 3), the swept laser 47 is first reflected off the dichroic beamsplitter 94 toward and through dichroic beamsplitter 93, the dichroic beamsplitters 94, 93 being aligned, as shown. The dichroic beamsplitter 94 is not necessarily needed when photoacoustic imaging is not part of the apparatus—even though it is shown as being employed in FIG. 4—because it can be appreciated from FIG. 4 that the OCT system 20 could be connected to the upper perimeter of the component platform 14 to direct the swept laser 47 directly down through the dichroic beamsplitter 93 onto galvo scanner 60. The dichroic beamsplitter 94 is a longpass filter blocking wavelengths below λ4 and allowing for passage of wavelengths above λ4. The dichroic beamsplitter 93 is a longpass filter blocking wavelengths below λ3 and allowing for passage of wavelengths above λ3. Thus, the swept laser 47 of wavelength between λ3 and λ4 reaches the galvo scanner 60 after being reflected off the dichroic beamsplitter 94 and passing through the dichroic beamsplitter 93 aligned with the galvo scanner 60.

The path of the swept laser 47 from the swept laser source 102, through the reference arm 98, to the mirror 101 and back to the OCT detector 105 matches the length of the path of the swept laser 47 from swept laser source 102, through the sample arm 97 to the tissue T and its reflected portion back to the OCT detector 105. This is achieved by having an appropriate length of cable carrying the swept laser in the reference arm 98, as shown at coil 107 and/or adjusting the distance between fiber collimator 72 and the mirror 101. The swept laser source 102 and the sample and reference arms form a frequency-domain OCT system. The returned lights from the sample arm 97 and the reference arm 98 interfere with each other to generate an interferogram. By scanning the laser wavelength a z-scan is obtained. By scanning the galvo scanner, a 2-D or 3-D OCT image can be obtained. The OCT system, with processor 26 (or other processor) works as known in the art to provide OCT imaging.

In some embodiments, the OCT system 20 consists of a fiber optic Michelson interferometer.

The FL excitation system 22 launches a blue laser with a wavelength below λ1 (e.g., 450 nm), represented by laser 48. The laser 48 is focused into an optical fiber 38 of the fiber bundle 32 as directed by the galvo scanner 60, and propagates to the tissue through the probe 12 or 112. The laser 48 excites the endogenous and exogenous fluorophores in the tissue T that is in contact with the distal end of the probe 12 or 112. The excitation can be implemented fiber-by-fiber (through a sequential imaging mode), in which case a full spectrum of the fluorescent emission can be obtained for each fiber using a spectrometer. The excitation can also be done on multiple or all pixels by defocusing through the fiber collimator 76, in which case a two-D fluorescent intensity image can be obtained with a CCD camera. The use of the spectrometer or CCD is shown at 109 of the FL emission system 24.

The blue laser source 111 is connected to the component platform 14 at a connector 113, and the laser 48 is directed through a fiber collimator 75 toward the dichroic beamsplitter 91. The dichroic beamsplitter 91 is a longpass filter allowing for passage of wavelengths above $\lambda 1$, such that the laser 48 with a wavelength below $\lambda 1$ is reflected to dichroic beamsplitter 92, with which dichroic beamsplitter 91 is aligned. Because dichroic beamsplitter 92 blocks wavelengths below $\lambda 2$, the laser 48 is further reflected to dichroic beamsplitter 93 with which dichroic beamsplitter 92 is aligned. Similarly, because dichroic beamsplitter 93 blocks wavelengths below $\lambda 3$, laser 48 is further reflected to galvo scanner 60 and directed to the tissue through the fiber collimator 76 and the probe 12 or 112. The tissue sample will provide a fluorescent emission 49 that is carried back through the fiber 38 or imaging bundle 32, to and through the fiber collimator 76, and reflected back off the galvo scanner toward the dichroic beamsplitter 93.

The fluorescent emission 49 has a wavelength between $\lambda 1$ and $\lambda 2$ such that it is reflected by dichroic 93 and dichroic beamsplitter 92 to pass through dichroic beamsplitter 91 to be reflected by mirror 114 to the CCD image sensor or spectrometer represented at 109, depending on which is employed. A band pass filter 115 and lens 116 are used to appropriately filter the emission spectrum and focus it onto the CCD image sensor or spectrometer represented at 109. The data collected at 109 can be analyzed and used to produce images through the processor 26 and appropriate hardware, software, firmware, etc.

Figure 7:
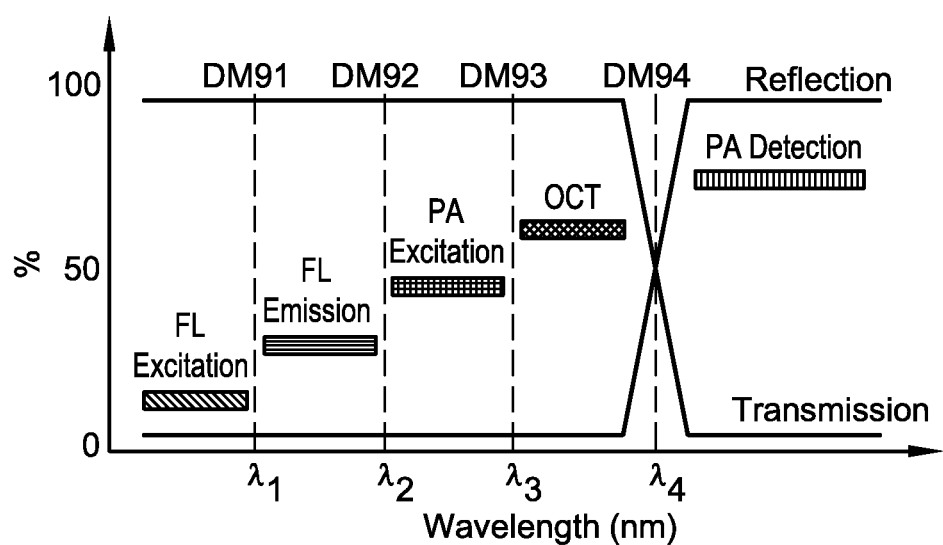
FIG. 7 is a graph showing the properties of the various wavelengths employed by the light sources of the various modalities, also relating them to the longpass filtering of the dichroic beamsplitters.

FIG. 7 provides a graph showing the properties of the various wavelengths employed by the light sources of the various systems, also relating them to the dichroic beamsplitters. Therein, the letters DM precede the numeral used to designate the specific dichroic beamsplitter in FIG. 1. The "Reflection" and "Transmission" lines show the characteristics of the first and second dielectric mirrors 42, 44. In general, the mirrors pass all wavelengths shorter than $\lambda 4$, but reflect a significant portion (50-95%) of wavelengths above $\lambda 4$.

In some embodiments, the apparatus is modular. Particularly, any one or more the tunable laser source 84, the amplified InGaAs photodiode 87, the swept laser source 102, the OCT detector 105, the pulse laser source 80, and blue laser source 111 can be switched out for a light source of differing wavelength, a photodiode of different responsivity, bandwidth or gain, or an OCT detector with different responsivity, bandwidth or gain, at any one of their respective connectors 85, 89, 103, 106, 81, 113. Such a design significantly improves the flexibility in selection of the source and detection systems for different clinical or biological applications In light of the foregoing, it should be appreciated that the present invention significantly advances the art by providing a multimodal endoscope apparatus that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A multimodal endoscope apparatus comprising:
    a multimodal endoscope probe including a fiber optic imaging bundle including a multitude of optical fibers;
    a galvo scanner and fiber collimator that are together capable of directing light to a single optical fiber of said multitude optical fibers;
    an optical coherence tomography system launching a swept laser to the galvo scanner, wherein said optical coherence tomography system includes a swept laser source and an optical tomography detector; and
    a fluorescence imaging system including:
    a fluorescence excitation system launching a fluorescence excitation laser to the galvo scanner, and
    a fluorescence emission system receiving a reflected fluorescence emission from the multimodal endoscope probe,
    wherein said swept laser is split at a coupler and directed (1) through a sample arm of said optical coherence tomography system to said galvo scanner, and (2) through a reference arm of said optical coherence tomography system directing light to a mirror for reflection back to said optical coherence tomography detector, and wherein said swept laser has a wavelength of from $\lambda 3$ to $\lambda 4$, and said swept laser in said sample arm is directed to a first dichroic beamsplitter on a path to said galvo scanner, wherein said first dichroic beamsplitter blocks wavelengths below $\lambda 3$ and allows for passage of wavelengths above $\lambda 3$, wherein $\lambda 3$ is less than $\lambda 4$ such that said swept laser passes through said first dichroic beamsplitter.

2. The multimodal endoscope apparatus of claim 1, wherein said swept laser in said sample arm is directed to a fourth dichroic beamsplitter, wherein said fourth dichroic beamsplitter blocks wavelengths below $\lambda 4$ and allows for passage of wavelengths above $\lambda 4$ such that said swept laser is reflected by said fourth dichroic beamsplitter toward said first dichroic beamsplitter.

3. The multimodal endoscope apparatus of claim 2, wherein the path of said swept laser from said swept laser source through said reference arm and back to said optical coherence tomography detector matches the length of the path of said swept laser from said swept laser source through said sample arm and to and through said multimodal endoscope probe to contact with a tissue and back to said optical coherence tomography detector.

4. The multimodal endoscope apparatus of claim 3, wherein said multimodal endoscope probe includes:
    a Fabry-Perot interferometer abutting a distal end of a fiber optic imaging bundle including a multitude of optical fibers, said Fabry-Perot interferometer including a polymer film sandwiched between a first dielectric mirror and a second dielectric mirror, wherein said first and second dielectric mirrors are transparent to the wavelengths produced from said optical coherence tomography system and said fluorescence imaging system.

5. The multimodal endoscope apparatus of claim 4, further comprising:
    a photoacoustic imaging system including:
    a photoacoustic excitation system launching a pulsed laser to the galvo scanner, and a photoacoustic detection system launching a interrogating laser to the galvo scanner.

6. The multimodal endoscope apparatus of claim 5, wherein said first and second dielectric mirrors reflect a portion of wavelengths from said interrogating laser.

7. The multimodal endoscope apparatus of claim 6, wherein said photoacoustic excitation system includes a pulsed laser source directing said pulsed laser to said galvo scanner.

8. The multimodal endoscope apparatus of claim 7, wherein said pulsed laser emits light at a wavelength of from $\lambda 2$ to $\lambda 3$, and said pulsed laser source directs said pulsed laser to said first dichroic beamsplitter, such that said pulsed laser is reflected by said first dichroic beamsplitter to said galvo scanner.

9. The multimodal endoscope apparatus of claim 8, wherein said pulsed laser source directs said pulsed laser to a second dichroic beamsplitter, such that said pulsed laser passes through said second dichroic beamsplitter to said first dichroic beamsplitter.

10. The multimodal endoscope apparatus of claim 9, wherein photoacoustic detection system includes an interrogating laser source directing said interrogating laser to said galvo scanner.

11. The multimodal endoscope apparatus of claim 10, wherein said interrogating laser emits light at a wavelength of greater than $\lambda 4$, and said interrogating laser source directs said interrogating laser to said first dichroic beamsplitter, wherein $\lambda 4$ is greater than $\lambda 3$ such that said interrogating laser passes through said first dichroic beamsplitter to said galvo scanner.

12. The multimodal endoscope apparatus of claim 11, wherein said interrogating laser source directs said interrogating laser to said fourth dichroic beamsplitter such that said interrogating laser passes through said fourth dichroic beamsplitter to said first dichroic beamsplitter.

13. The multimodal endoscope apparatus of claim 12, wherein said photoacoustic detection system further comprises an amplified InGaAs photodiode, and said interrogating laser is received by said amplified InGaAs photodiode.

* * * * *